(12) United States Patent
Termanini

(10) Patent No.: US 10,398,560 B2
(45) Date of Patent: Sep. 3, 2019

(54) SYSTEM AND METHOD FOR SIDE INSERTION OF A BICONDYLAR MINI KNEE IMPLANT

(71) Applicant: Joint Innovation Technology, LLC, Boca Raton, FL (US)

(72) Inventor: Zafer Termanini, Port Saint Lucie, FL (US)

(73) Assignee: JOINT INNOVATION TECHNOLOGY, LLC, Boca Raton, FL (US)

( * ) Notice: Subject to any disclaimer, the term of this patent is extended or adjusted under 35 U.S.C. 154(b) by 0 days.

(21) Appl. No.: 16/040,147

(22) Filed: Jul. 19, 2018

(65) Prior Publication Data

US 2018/0325686 A1    Nov. 15, 2018

Related U.S. Application Data

(62) Division of application No. 15/096,209, filed on Apr. 11, 2016, now abandoned.

(51) Int. Cl.

| | |
|---|---|
| *A61F 2/38* | (2006.01) |
| *A61B 34/20* | (2016.01) |
| *A61B 34/30* | (2016.01) |
| A61B 17/15 | (2006.01) |
| A61B 17/00 | (2006.01) |
| A61B 17/16 | (2006.01) |
| A61B 17/17 | (2006.01) |

(52) U.S. Cl.
CPC ............ *A61F 2/3859* (2013.01); *A61B 34/20* (2016.02); *A61B 34/30* (2016.02); *A61F 2/38* (2013.01); *A61F 2/389* (2013.01); *A61B 17/155* (2013.01); *A61B 17/157* (2013.01); *A61B 17/1675* (2013.01); *A61B 17/1764* (2013.01); *A61B 2017/00734* (2013.01); *A61B 2034/2065* (2016.02); *A61F 2220/0016* (2013.01); *A61F 2310/00011* (2013.01)

(58) Field of Classification Search
CPC ..................... A61G 13/0063; A61G 13/0081
See application file for complete search history.

(56) References Cited

U.S. PATENT DOCUMENTS

| | | |
|---|---|---|
| 4,224,696 A | 9/1980 | Murray et al. |
| 4,309,778 A | 1/1982 | Buechel et al. |

(Continued)

FOREIGN PATENT DOCUMENTS

WO    2010040905 A1    4/2010

*Primary Examiner* — Megan Y Wolf
(74) *Attorney, Agent, or Firm* — Norris McLaughlin PA

(57) ABSTRACT

A bicondylar knee implants with improved fixation means for resurfacing only the weight-bearing surface of the femoral medial and lateral condyles, while preserving the cruciate ligaments and avoids displacing the patella. The inventive device includes metallic convex articular surfaces for resurfacing the medial and lateral femoral condyles, and concave multifacial non-articular surfaces to be affixed to the resected distal surfaces of the femur. The prosthesis provides claws situated at the anterior and posterior ends of the medial and lateral metallic condyles, which will firmly attach the implant against the resected femoral condyle. The prosthesis is designed to be implanted through a direct lateral approach and does not resurface the femoropatellar joint. Furthermore, a minirobot or electromechanical actuator is used to perform the femoral and tibial bone cuts using electromagnetic bone chipper.

7 Claims, 15 Drawing Sheets

(56) References Cited

U.S. PATENT DOCUMENTS

| | | | |
|---|---|---|---|
| 4,470,158 | A | 9/1984 | Pappas et al. |
| 4,659,331 | A | 4/1987 | Matthews et al. |
| 6,197,064 | B1 | 3/2001 | Haines et al. |
| 6,299,645 | B1 | 10/2001 | Ogden |
| D473,307 | S | 4/2003 | Cooke |
| 6,726,724 | B2 | 4/2004 | Repicci |
| 7,141,053 | B2 | 11/2006 | Rosa et al. |
| 7,695,520 | B2 | 4/2010 | Metzger et al. |
| 8,114,164 | B2 | 2/2012 | Termanini |
| 8,167,883 | B2 | 5/2012 | Termanini |
| 9,192,459 | B2 | 12/2015 | Cheal et al. |
| 2008/0119939 | A1 | 5/2008 | Termanini |
| 2009/0198341 | A1 | 8/2009 | Choi et al. |
| 2016/0081758 | A1 | 3/2016 | Bonutti |

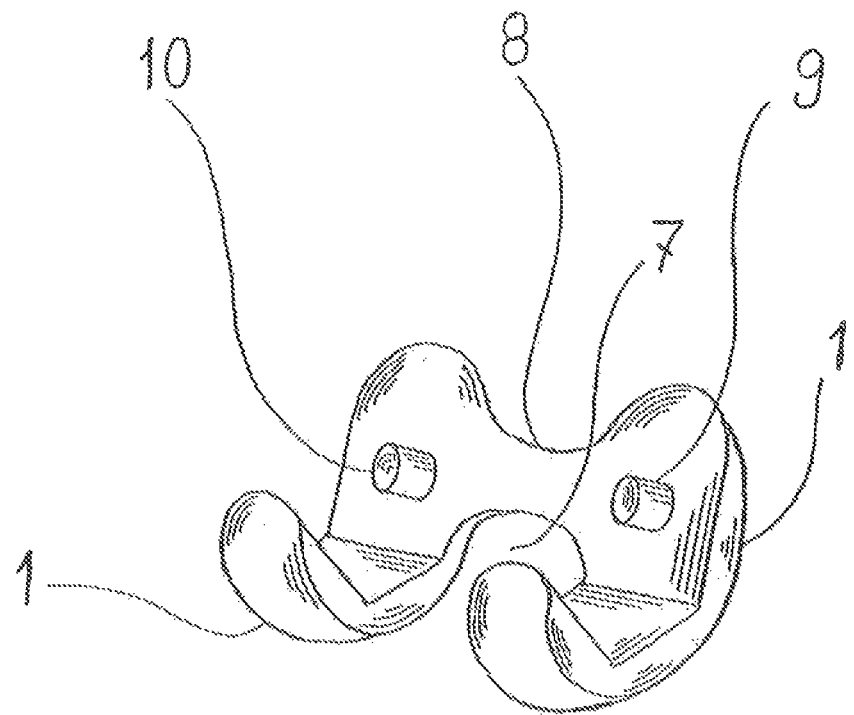
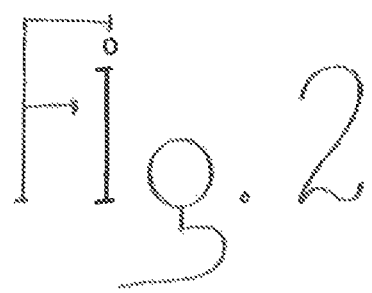

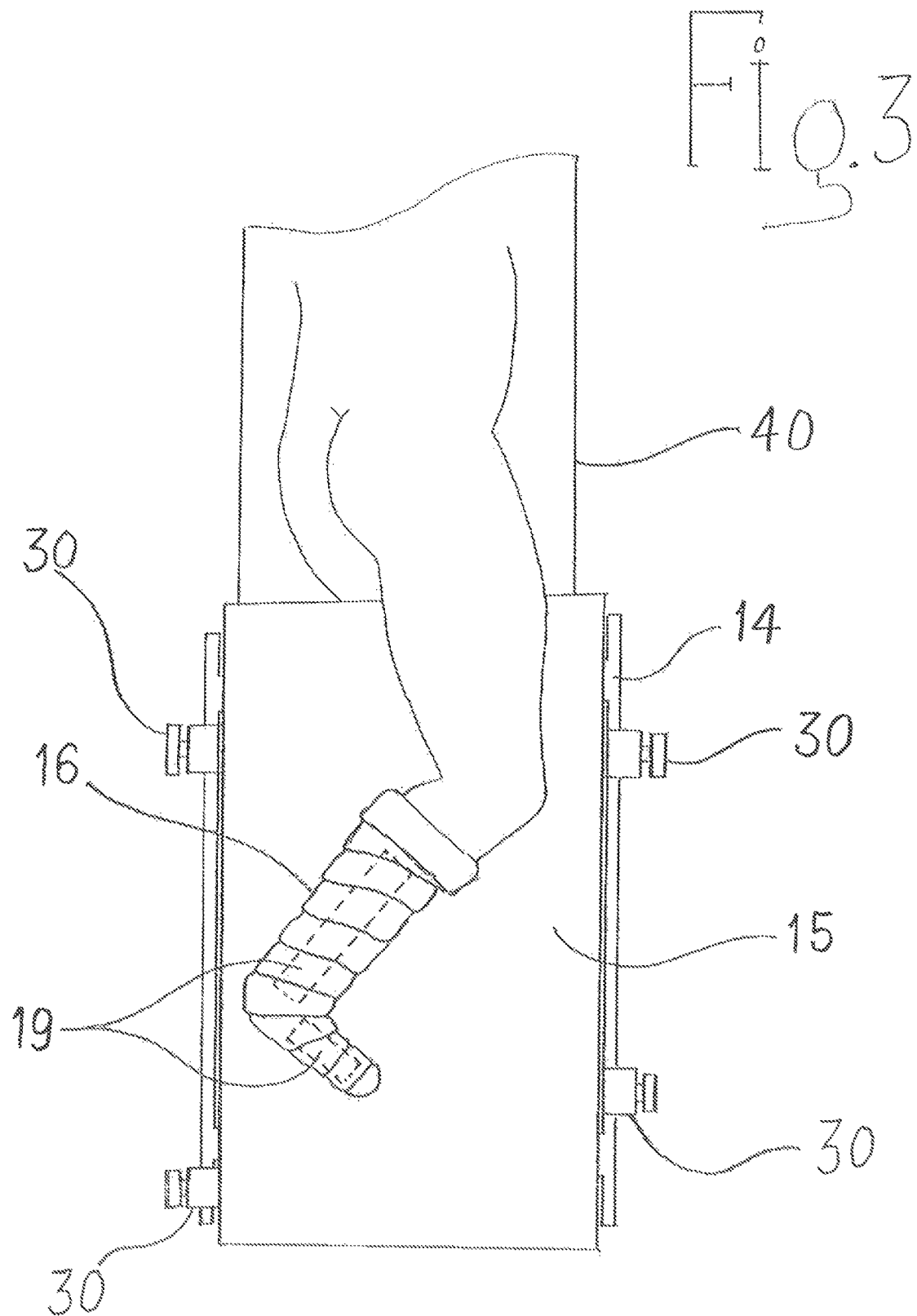

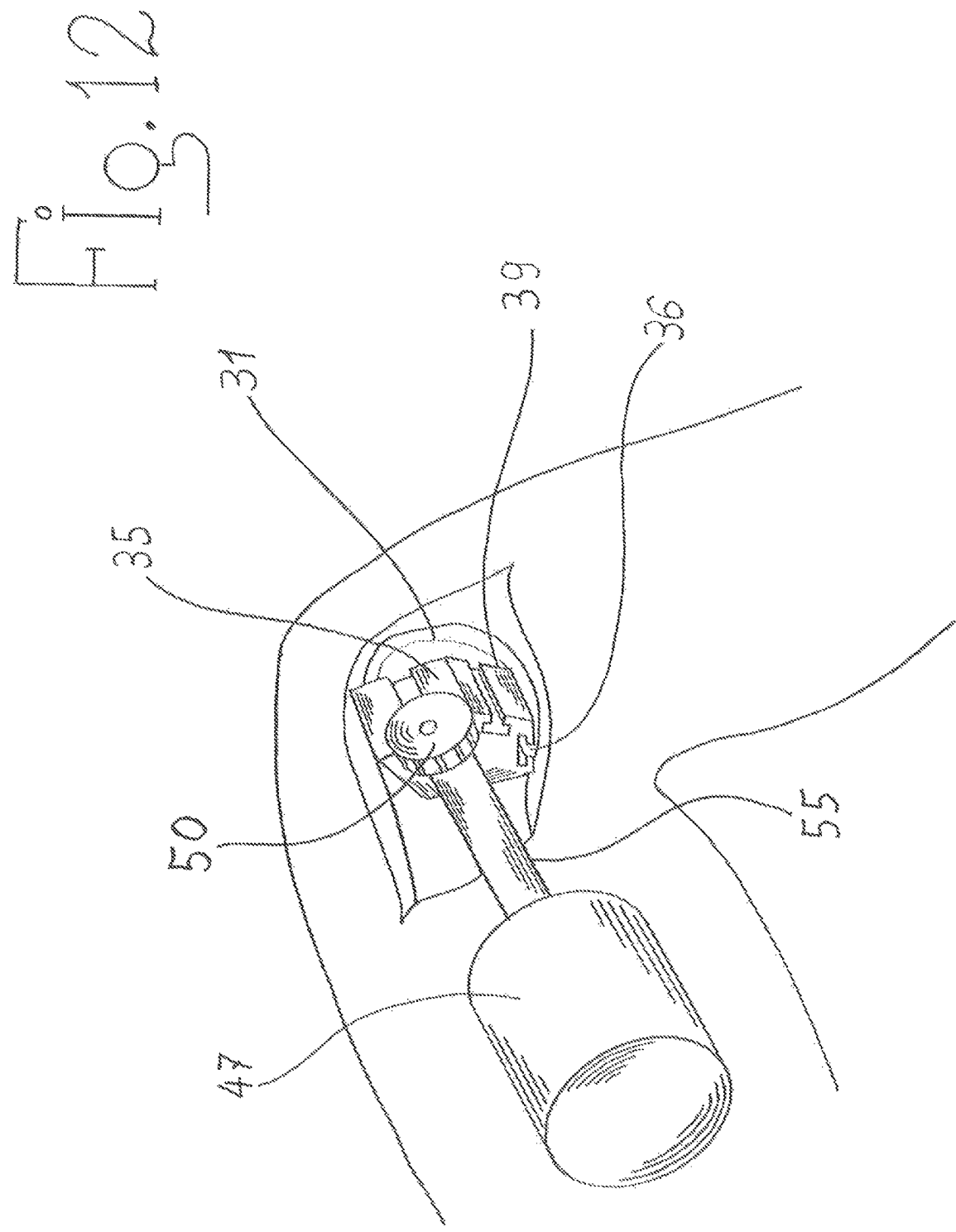

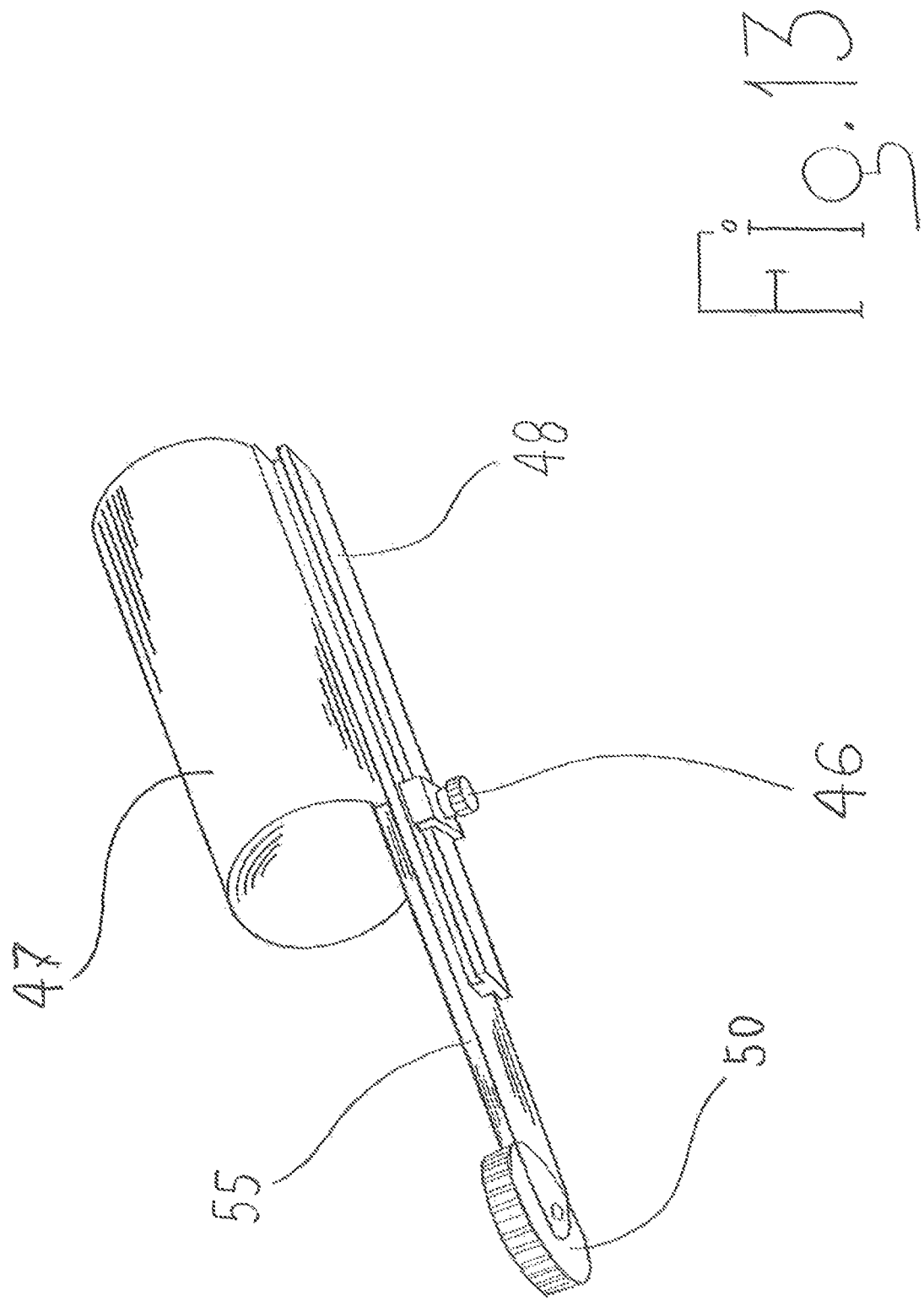

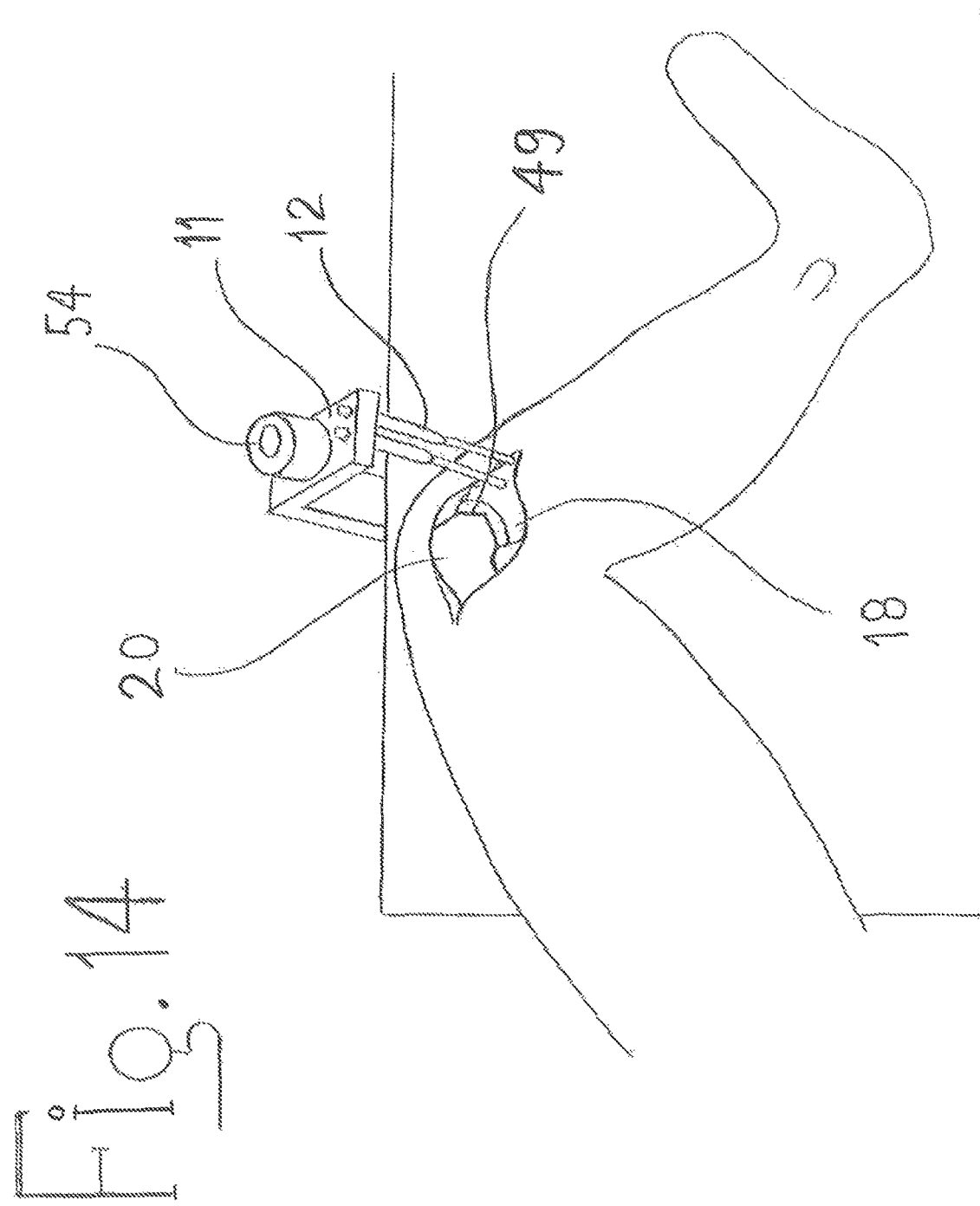

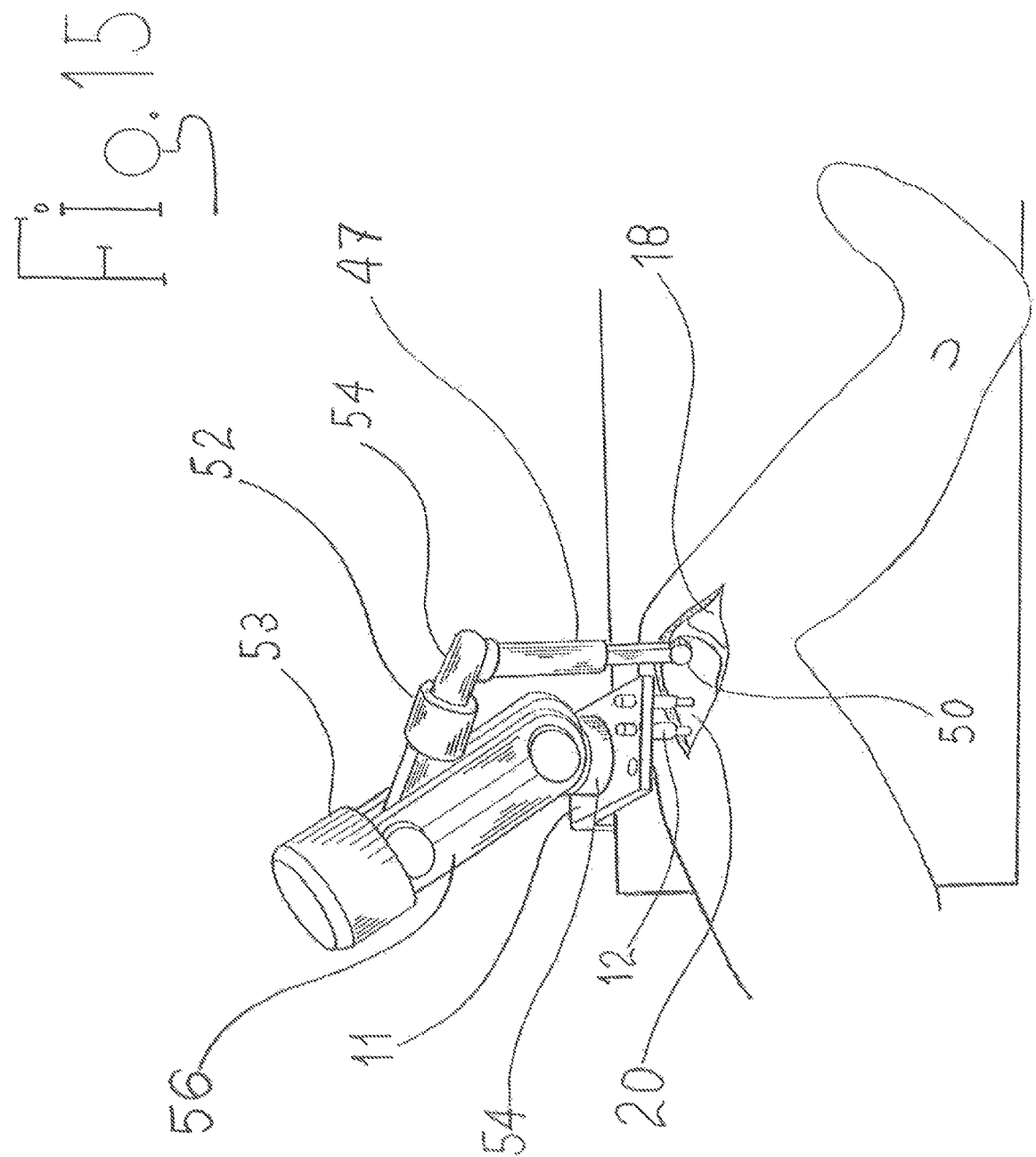

SYSTEM AND METHOD FOR SIDE INSERTION OF A BICONDYLAR MINI KNEE IMPLANT

This is a Divisional patent application of U.S. Ser. No. 15/096,209 filed 11 Apr. 2016, and claims all available priority benefit thereto, and the entirety of which prior application is hereby incorporated by reference.

BACKGROUND OF THE INVENTION

The present invention relates generally to a resurfacing prosthesis and more specifically it relates to an improved side sliding mini knee prosthesis used for the resurfacing of articular surfaces of tibia and femur, and a surgical method for insertion of said mini implant through a small and minimally invasive direct lateral approach, using templates and a miniature robotic actuator cutting device, without any disruption of extensor mechanism, quadriceps tendon or damage to the cruciate ligaments.

It can be appreciated that knee arthroplasty and resurfacing knee implants have been in use now for many decades. The procedure usually requires the operating surgeon to prepare the end of the tibial and femoral bones to receive the implant. This preparation requires the careful removal of the articular surface and adjacent bone in order to receive the intended implant.

Said preparation requires the use of mechanical bone resection devices such as mills, bone saws or high-speed burrs. In order to accomplish such task, the operating surgeon needs to expose the bone end and protect the surrounding tissue from the aggressive cutting tools.

Typically, knee replacement prostheses comprise several types of implants, where articular surfaces of the knee are removed and replaced with metal and polyethylene components. There has been little change to the basic design of the femoral and tibial components as well as surgical insertion techniques since the initial inception in the mid fifties.

The devices of the prior art attempted to duplicate the geometry of the natural articular femoral and tibial surfaces, where the femoral component have a semicircular C shaped implant device such as depicted in a U.S. Pat. No. 4,224,696. The bicondylar design is similarly disclosed in prior patents by F. Buechel and Pappas in U.S. Pat. Nos. 4,309,778 and 4,470,158. A more recent bicondylar design is described in U.S. Pat. No. D473,307S and U.S. Pat. No. 6,197,064 B1. The prior art describes the bicondylar prosthesis as having a middle patellar groove for the femoropatellar articulation. Other knee implant devices are used to resurface only one femoral condyle such as unicondylar prosthesis described in U.S. Pat. No. 7,141,053; 6,726,724 B2.

The majority of the commonly used knee implants use bone cement as a mean of fixation to the bone. More recently, cementless and bone ingrowth fixation has been introduced and used for the tibial, femoral and patellar surfaces.

Other prior art includes bicondylar resurfacing implant, such as the one described in U.S. Pat. No. 8,114,164 by Zafer Termanini. However, said implant did not allow the use of bone cement as mean of fixation and relied solely on geometry interference between the transverse ridges and the resected bone surfaces. The implant of the present invention will allow the use of bone cement, while still specifically introduced through direct lateral approach.

However, unicondylar implants in general present a high rate of failure due to loosening and dislocation secondary to poor distribution of weight and high concentration of stress over a small surface. Furthermore, almost all the described implants in the above-cited patents are inserted through the invasive conventional anterior approach. Such a surgical approach causes extensive soft tissue disruption and irreparable scarring to major anatomical structures.

Another problem with the conventional surgical approach is the fact that the femoral condyles are approached anteriorly through a medial or lateral parapatellar approaches requiring to laterally displace the patella or dislocate ("flip over") the patella in order to approach and expose the distal end of the femur and to better visualize the medial and lateral surfaces to be cut. Said dislocation ("flip over") or lateral displacement of the patella, frequently weakens and damages the insertion of the patellar tendon, causing undue pain in the immediate postoperative period and lengthens post operative physical therapy. Typically, the operating surgeons commonly extend the incision or cut ("snip") the Vastus medialis muscle in order to facilitate the lateral displacement of the patella. Furthermore, the large sizes of the conventional femoral and tibial components make them difficult to insert through a small and limited incision of the direct lateral approach. The prosthesis of this invention is thinner and much smaller than the conventional total knee femoral component, since it does not resurface the femoropatellar joint.

While conventional devices may be suitable for the particular purpose to which they address, they are, because of their size, not suitable for bicondylar knee resurfacing through a limited direct lateral approach, without disrupting the extensor mechanism, damaging the quadriceps tendon or the cruciate ligaments.

During a conventional total knee replacement, the distal femur is usually resected with five cuts that correspond to the shape of the inner surface of the femoral component. These cuts are commonly performed with a bone-cutting tool, such as a power oscillating saw or a mill that is guided by a cutting block or a template affixed to the bone through the anterior approach. Said cutting block provide slots that are at fixed distances and angles from one another so that one cutting block must be provided for each size and shape of the implant. The plane of the slot is also fixed so it cannot be modified once the block is affixed to the bone. The accuracy of the cut is proportional to how steady is the hand of the surgeon as well clearance of the blade in the slot. The blade is flexible and can bend if levered in the slot causing the cutting tip of the blade to deflect. This will lead to a change in the plane of the cut and subsequently lead to discrepancy in the press fit of the implant. Obviously, this is more significant and crucial for non-cemented implants.

In these respects, the bicondylar knee resurfacing prosthesis according to the present invention substantially departs from a conventional concepts and designs of the prior art, and in so doing provides an implant that is specifically designed to be inserted through a mini direct true lateral approach without any damage to the patellar tendon, quadriceps mechanism or the cruciate ligaments.

A significant advantage provided by the System of this invention is in using an electromagnetic bone chipper device guided by surgical polygonal cutting blocks having an inverted T slots or channels rather than straight slots. Said inverted T channels are much more precise than the straight slots of conventional cutting blocks. Furthermore, the shank of the electromagnetic bone chipper device used to perform the bone resection is thicker and will not deflect or bend if accidently levered by the operating surgeon.

SUMMARY OF THE INVENTION

In view of the forgoing disadvantages inherent in the known types of knee resurfacing prostheses now present in the prior art, the present invention provide a new implant having medial and lateral condylar knee resurfacing construction wherein the same can be inserted through a small direct lateral approach without disruption of a extensor mechanism or damage to the quadriceps tendon and without addressing the femoropatellar articulation.

The general purpose of the present invention, which will be described subsequently in greater detail, is to provide a new bicondylar knee resurfacing prosthesis that has many advantages of the prior knee resurfacing prostheses and many novel features that result in a new mini condylar knee resurfacing prosthesis which is not anticipated, rendered obvious, suggested, or even implied by any of the prior art knee resurfacing prosthesis, either alone or in any combination thereof.

Furthermore, The present invention delineate a method for inserting the new bicondylar knee implant through a limited and minimally invasive direct lateral approach to the knee without causing any damage to the quadriceps tendon and the surrounding soft tissue using guided electromechanical bone chipper/mill introduced laterally into the knee as opposed to the commonly used anterior approach, where articular surfaces of the femur and tibia are accessed from the front after displacing the patella medially.

To attain this, the implant of the present invention generally comprises a metallic femoral component having geometry to match the weight bearing portion of both medial and lateral femoral condyles, a metallic tibial tray having geometry to match weight bearing portion of the tibial plateau and a polyethylene tibial insert.

The metallic femoral component having a curved arcuate polished convex articular surface in a form of two condyles, medial and lateral, which are connected together distally by a non-articulating bridge. The concave surface has a femoral fixation means in a form of a transverse hook or straight metallic transverse retaining claws. Said claws are located at either end of the medial and lateral condyles.

A metallic tibial tray, which will also be inserted laterally through a mini incision in the lateral quadrilateral space as delineated in FIG. 7, has a bottom surface to be affixed to the tibial plateau that has been surgically prepared. Said bottom surface has a fixation means in the form of retaining claws. Said retaining claws means extends transversely along the entire width of the metallic tray at the front and back of said tibial tray. The top surface provides retaining lips for the purpose of holding the polyethylene tibial insert. Said retaining lips are positioned transversely along the entire width of the metallic tray so that the polyethylene tray can be slidingly inserted laterally through a mini incision in the lateral quadrilateral space.

Once slid into position in the tibial tray, the polyethylene insert will be firmly retrained by a locking mechanism comprising a small recess in the metallic tibial tray and a corresponding protruding tang provided at the bottom of the polyethylene tray. This will allow the polyethylene component to lock in place after complete insertion and prevents it from moving out once it is locked in.

During the surgical procedure, the patient is placed on his side with the operated knee placed onto a surgical platform firmly attached to the side rails of the operative table. The operated lower extremity is then secured to the platform by one of several means such as a conventional vacuum "bean Bag positioner". Vacuum bean bags positioners are commonly used to immobilize patients or extremities securely and comfortably during surgical procedures. Said bags such as MEDVAC brand bean bag positioner immobilizers are readily available in operative rooms. If the operating surgeon wishes to move the leg then the vacuum in the "Bean Bag" is deflated and the lower extremity is then released to be freely move.

Other means of fixation would be the use of strong commercial grade wide VELCRO that will firmly stick to the stockinet wrapped around the lower leg and hold the leg firmly attached to the platform. It is clearly appreciated that it is easier to perform surgery on the lateral surface of the knee when patient is in the lateral decubitus position which eliminates the effect of gravity, which requires a cumbersome knee holder device and an assistant to hold the leg in flexion during the conventional anterior approach, where patient is placed on his back in supine position.

Other means of fixation of the lower leg would be the use of a mechanical vise that can be firmly attached to the operating table.

After the appropriate positioning of the lower leg on the operative platform and secured with Vacuum Beanbag or VELCRO (as shown in FIG. 3) the operating surgeon will make a small skin incision over the lateral aspect of the knee in the quadrilateral space and expose the lateral anatomical structures of the knee. Flexion of the knee to about 90 degrees will displace the ileotibial band and the lateral collateral ligament posteriorly away from the surgical field. No other anatomical structure remains in the quadrilateral space. The fascia and retinaculum are incised and the lateral condyle of the knee is exposed. Subsequently, the patella is minimally elevated from the femoral condyles and maintained separated using a patellar self-retaining device. It is to be noted that at no time the patella is retracted, everted or displace medially or laterally. The quadriceps muscle and the extensor mechanism remain intact at all time.

In one embodiment, the bone resection process is accomplished using a bone chipper or cutting tool as fully described in U.S. Pat. No. 8,167,883 by Zafer Termanini and with external bone cutting templates. Said templates are affixed to the lateral aspect of the distal tibia and femur by two fixation pins. For accurate placement of the fixation pins over the lateral aspect of the distal femur, a hand held condylar template is used (FIG. 4). Said condylar template will sit on the convex articular surface of the femoral condyle. In doing so, the hand held condylar template, through a mini outrigger, will allow insertion of two fixation pins at a predetermined angle and strictly parallel to the resection surface.

The above described fixation pins will be used to align the external polygonal cutting blocks (FIG. 6), where the inverted T channel will be used to guide the electromagnetic bone chipper device 47 during bone resection and surface preparation.

In another embodiment of the present invention, the above-described retaining claws are replaced with one or more short post centrally located over the larger flat non-articulating concave surface of the medial and lateral condyles (FIG. 2). The presence of these posts will prevent the medial or lateral migration of the implant after insertion. This modified mini implant, in this embodiment, can still be inserted laterally through a mini incision in the lateral quadrilateral space. However, this improved implant will allow the use of conventional bone cement as a mean of fixation.

In another embodiment of the present invention, the preparation of the distal femur and proximal tibia for insertion of the femoral and tibial components is performed using an electromechanical cutting device similar to that disclosed in U.S. Pat. No. 8,167,883 issued on May 1, 2012 to Zafer Termanini:

In accordance with still further aspects of this invention, said electromechanical cutting device can be attached to an computerized electromechanical actuator or mini robot programmed to precisely perform the femoral and tibial cuts and bone resection by feedback from a CT scan of the patient. The main advantage of this motorized actuator over the conventional orthopedic techniques is improved accuracy and precision in the preparation of bone surfaces, more reliable and reproducible outcome, as well as greater spatial accuracy. The synchronized computerized system controlling said actuator would use DICOM data from pre-operative CT scan of the patient in order to delineate the precise location or the cuts. As opposed to other conventional robotic cutting systems where the computerized system is merely used to align the cutting templates or saw guiding slots, the actuator as described in the present invention does in fact precisely perform the cutting and bone resection itself without the use of cutting blocks or templates or any intervention from the operating surgeon. This does eliminate any imperfection or inconsistency related to poor cutting surgical techniques or deflections related to the saw blade.

The ability to isolate and rigidly fix bones in predetermined and known positions allow robotic devices to spatially be securely fixed to the bone. As such, the bone is treated as a fixed object simplifying the computer control of the robot/actuator. It is basically the same principle used in modem CNC machining. The robot/actuator-assisted surgery can achieve levels of accuracy, precision and safety not capable with computer-assisted navigation, since cutting is still performed manually by the operating surgeon.

To further stabilize the operated knee and lower extremity, two parallel pins are inserted into the lateral aspect of the distal femur at the proximal end of the surgical wound.

Said pins are firmly attached to a steady outrigger for the purpose of stabilizing the distal femur. Said outrigger is firmly attached to the side rails of the operating table with heavy brackets. This will provide solid support for the bone with respect to a reference structure.

Following the aforementioned step, wherein the femoral bone is firmly attached to operating table, the minirobot/actuator is utilized to perform the distal femoral cuts. Said actuator will be firmly attached to the top of the outrigger arm and will have at least four axis of freedom.

An electromagnetic bone chipper device as described in U.S. Pat. No. 8,167,883 or similar cutting device is attached to the distal arm of the electromechanical actuator in order to perform precise bone cuts at very specific planes Using Reverse Engineering Techniques known to the art, spatial registration of anatomical landmarks can be performed. Reverse engineering has become a viable method in the mechanical industry to create a 3D virtual model of an existing physical object for use in 3D CAD (computer aided design). Reverse engineering is also used in industry to bring existing physical geometry of an object into digital environment or to make a digital 3D record of a product. It is further understood that Reverse Engineering process creates a computer aided design model from scan data of a physical object. The process requires converting measured data into geometrical complexes surfaces.

To attain this objective, initial spatial registration of the actuator is required in relation to a solidly fixed reference point. In addition, a computer processor would then superimpose said reference point over the DICOM data obtained from the CT scan of the patient prior to surgery. The two aforementioned fixation pins geometrically provide a spatial plane that will be used for registration. The distance between the parallel pins will be used as physical scan data.

The preferred location of bone resection plane is determined and preoperatively registered on the CT scan by the operating surgeon. The resection planes are highlighted and information is then displayed on a monitor screen allowing the surgeon to visually confirm the actual orientation of the bone cut and approve the position and orientation of the bone cuts.

Some of the advantages of the present invention over the prior art prosthetic knee replacement is the fact that the bone chipper/cutter used to perform the bone resection has a circular shape that correspond to the circular shape of the cut surfaces of the femur and tibial bones The position, orientation and, more importantly, depth of the cutting planes are dictated by the controller, which receives coordinates both in space and scale from the CT scan.

Similar to the CAD/CAM systems and devices commonly used in the industry for the machining of prototypes and finished industrial parts, the processor of the present system uses DICOM data created by the CT scan of the patient to generate a tool path that drives the actuator and electromagnetic bone chipper device so it performs the bone resection accurately according to DICOM received from the CT scan.

Once the registration of the anatomical landmarks is complete, the distal arm of the minirobot along with the cutting tool is led to a reference point designated on the monitor and confirmed by the robot. The robot will then be allowed to perform the bone cuts under the direct supervision of the surgeon. The algorithm of the sequence is similar to the operation of a CNC machine, where the work piece is solidly fixed in a vise and the milling head will perform the cutting and shaping of the work piece.

There has thus been outlined, rather broadly, the more important features of the invention in order that the detailed description thereof may be better understood, and in order that the present contribution to the art may be better understood and appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a bicondylar knee resurfacing prosthesis for primarily resurfacing the weight bearing area of the knee joint that is limited to the arc of motion area between the tibia and the femur. Said prosthesis is inserted through a limited direct lateral approach, situated within the lateral quadrilateral space and without disruption of the extensor mechanism or damage to the quadriceps tendon.

The prosthesis described in this invention will overcome the shortcomings of the prior art devices. Other objects and advantages of the present invention will become obvious to the reader and it is intended that these objects and advantages are within the scope of the present invention.

While this invention may be embodied in the form illustrated in the accompanying drawings, attention is been called to the fact, however, that the drawings are illustrative only and not to scale, and that changes may be made in the specific construction illustrated.

SUMMARY DESCRIPTION OF THE DRAWINGS

Various objects, features and attendant advantages of the present invention will become fully appreciated as the same becomes better understood when considered in conjunction with the accompanying drawings, in which like references characters designate the same or similar parts throughout the several views, and wherein:

FIG. 2 is a perspective view of the femoral component in a different embodiment showing central miniposts.

FIG. 3 is a schematic illustration of the patient positioned in lateral decubitus on the operating table with split platform between legs. Lower leg been secured to the platform with stockinet and Velcro.

FIG. 12 is a perspective view of the electromechanical bone cutter, showing the T slotted cutting blocks with electromagnetic bone chipper device gliding into T slots.

FIG. 13 Is a perspective view of the electromechanical bone cutter, showing the T shaped rail and locking knob attached to the bottom of the device.

FIG. 14 Is a perspective view of the proximal tibia being attached to the outrigger with two fixation pins after distal femur articular surfaces been already resected.

FIG. 15 is a schematic illustration of the robotic electromechanical bone cutter and attachment to the operating table.

DETAILED DESCRIPTION OF THE INVENTION

Figure 1:
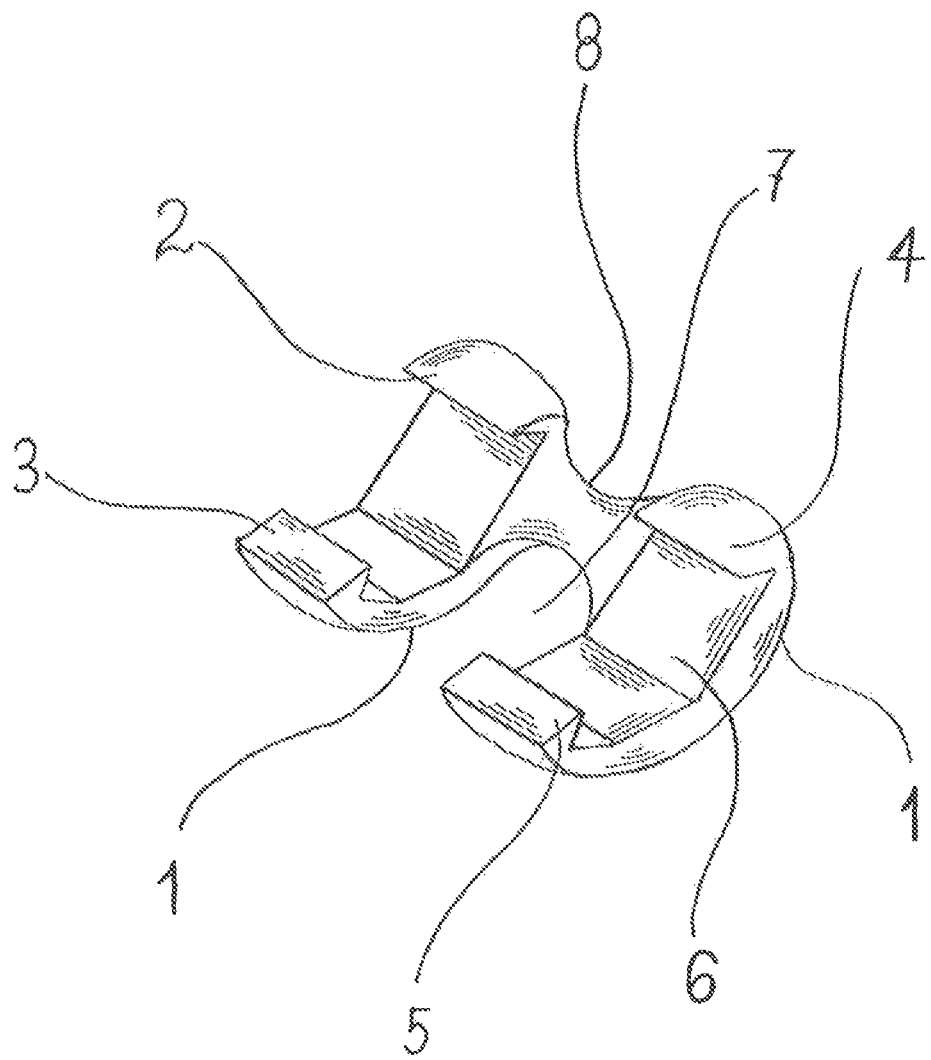
FIG. 1 is a perspective view of the femoral component showing the retaining claws.

Turning now descriptively to the drawings, in which similar references characters denote similar element throughout the several views, the attached figures illustrate a concise bicondylar knee resurfacing prosthesis, which comprises a thin metallic femoral arcuate component, a metallic tibial tray and a polyethylene tibial insert. Furthermore, the present invention provides a detailed description of the method to insert the mini bicondylar implant through a small surgical incision made over the lateral aspect of the operated knee away from the patella and without any disruption or damage to the quadriceps muscle or the patellar tendon.

As opposed to conventional surgical total knee replacement surgery, where the patient lies supine on his back, the surgical technique utilized in the present invention is performed with patient lying on his side on the operative table. The operated knee placed onto a surgical platform 15 firmly attached to the side rails of the operative table 40 with at least four adjustable brackets 30. The operated lower extremity is then secured to the platform using strong commercial grade wide VELCRO 19 that will firmly stick to the stockinet wrapped around the lower leg and hold the leg firmly attached to the platform.

To attain this objective, the present invention describes a method where an electromagnetic bone chipper device 47 is used to precisely perform the bone resection through the lateral approach. Such device is described in details in U.S. Pat. No. 8,167,883 of Zafer Termanini.

The femoral component (FIG. 1) of the bicondylar implant comprises two highly polished convex articular surfaces medial and lateral 1, that are connected anteriorly with an intercondylar connection 8, leaving a space or intercondylar interval 7, which will allow the cruciate ligaments to be preserved and retained.

The concave surface of the medial and lateral condyles have a metallic claws on either end of each condyle 2, 3, 4, 5 (FIG. 1). Said metallic claws have the shape of a recurve flange in its cross section and extend transversely along the entire width of each condyle, as depicted. Said metallic claws 2, 3, 4, 5 form an angle of 70 to 95 degrees with the posterior non-articulating adjacent surface 6 of the implant.

The length of the claws varies between 10 to 20 millimeters and measures approximately 7-12 millimeters thick at its base where it contacts the body of the femoral component. The tip of each claw is sharp, however, the side edges are rounded so they do not form any stress risers, which may cause bone damage and lead to osteolysis.

In another embodiment of the present invention, the metallic claws can have a parallel front and back surfaces and have a rounded blunt tip.

The concave surface of the present implant provides fine asperities and voids to allow bone ingrowth, which will solidly affix the femoral metallic component to bone. Said femoral metallic component can also, if need arise, be cemented to the femur 20 using conventional methyl methacrylate bone cement.

Figure 7:
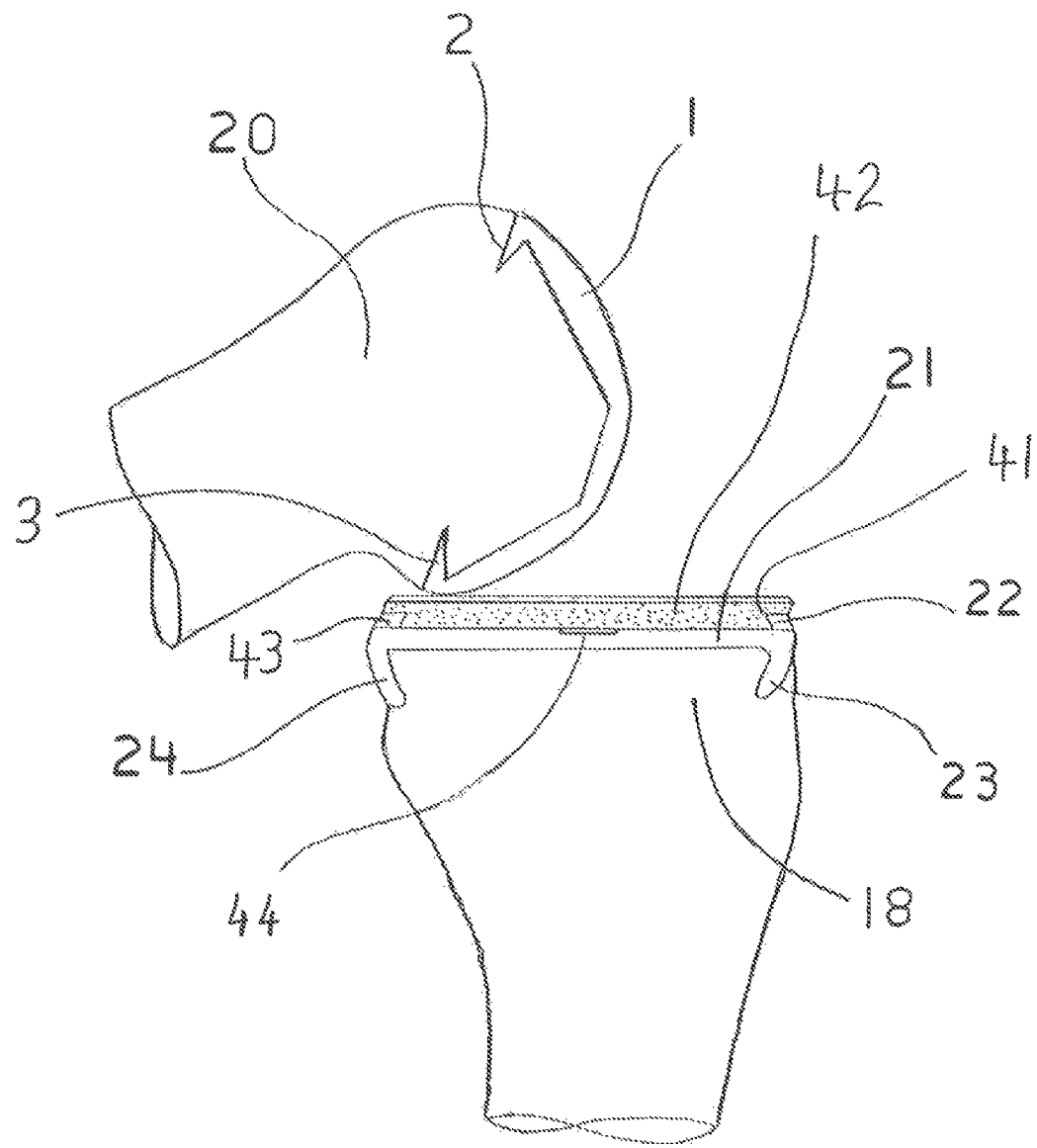
FIG. 7 is a sectional view of the femoral component inserted onto the distal femur and the tibial component inserted onto the proximal tibia.
Figure 8:
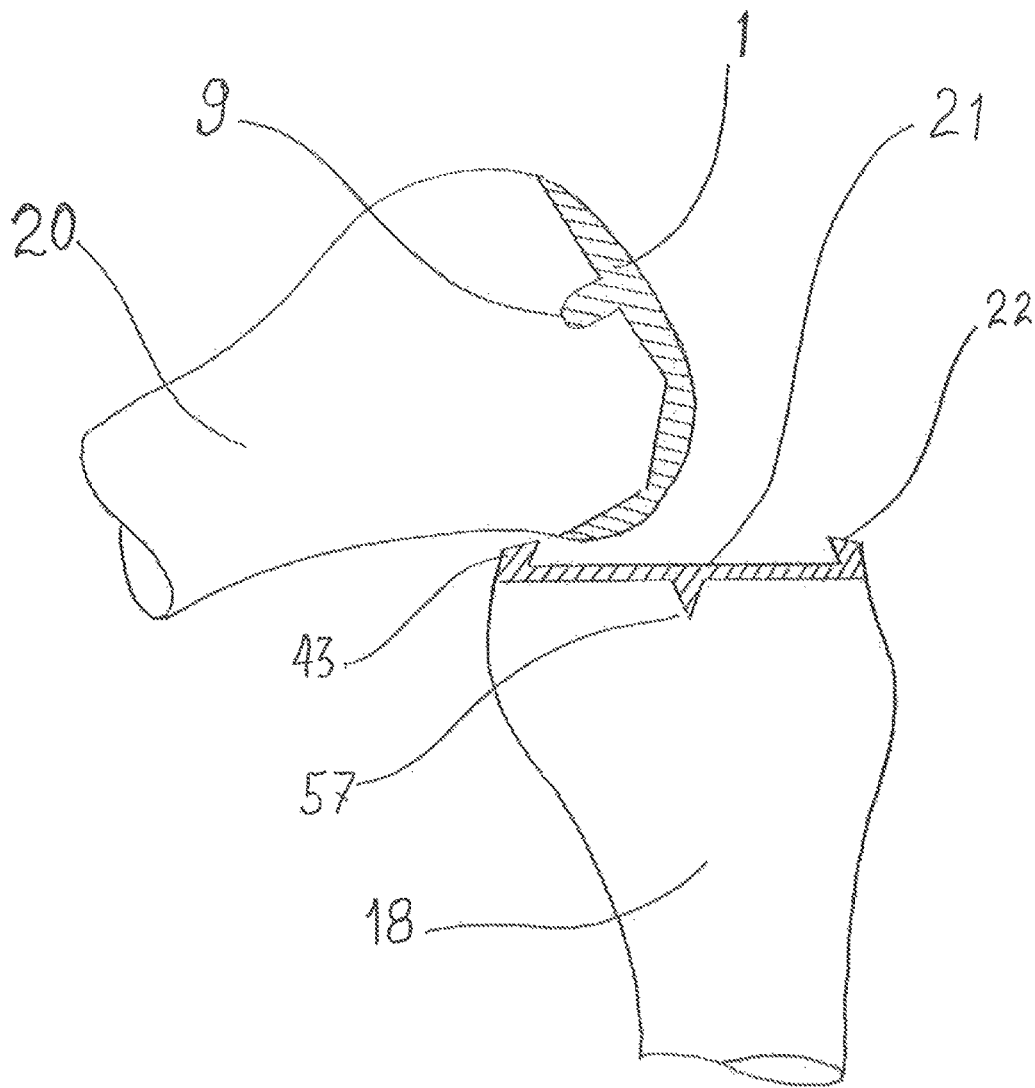
FIG. 8 is a sectional view of different embodiment of the femoral and tibial component with dull and sharp posts.

The metallic tibial tray 21 (FIG. 7) has a flat top and bottom surface. As shown in FIG. 7 and in FIG. 8, the bottom surface provides metallic downward extensions 23 and 24 in the form of claws for the purpose of securely retaining the metallic tibial tray to the tibia. Said metallic claws run transversely across the lower surface of the metallic tibial tray in the front 23 and the back 24 thereof. Once slid in place from the side, the claws will provide a strong mean of fixation of said tibial tray to the bony tibial plateau 18.

In a different embodiment of the present invention (FIG. 8), the aforementioned tibial claws can be replaced with at least two short miniposts 57, which may have sharp pointed tip to facilitate penetration into soft cancellous bone.

Figure 9:
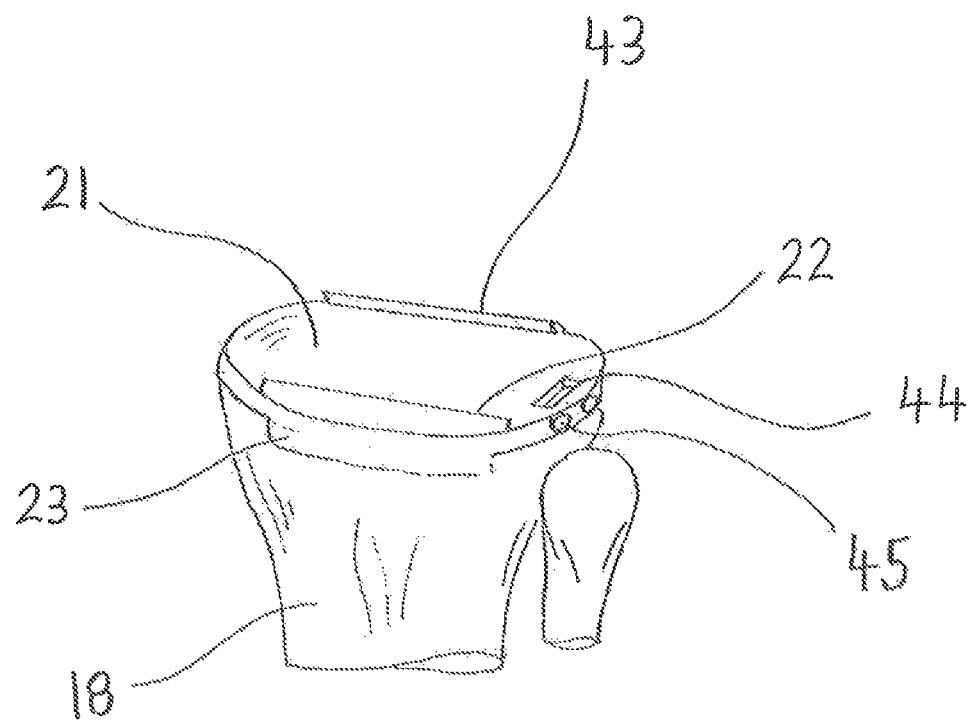
FIG. 9 is a perspective view of the metallic tibial component inserted onto the proximal tibia.

The top surface of the metallic tray, has an anterior 22 and posterior 43 metallic ridges having the shape of lips, each of which runs transversely across the entire width of the top surface of the metallic tibial tray 21, as shown in FIG. 7 and in FIG. 9.

The bottom surface of the tibial implant provides fine asperities and voids to allow bone ingrowth, which will solidly affix the tibial metallic component to tibial bone. Said tibial metallic component can also, if the need arises, be cemented to the tibia using conventional methyl methacrylate bone cement.

Figure 10:
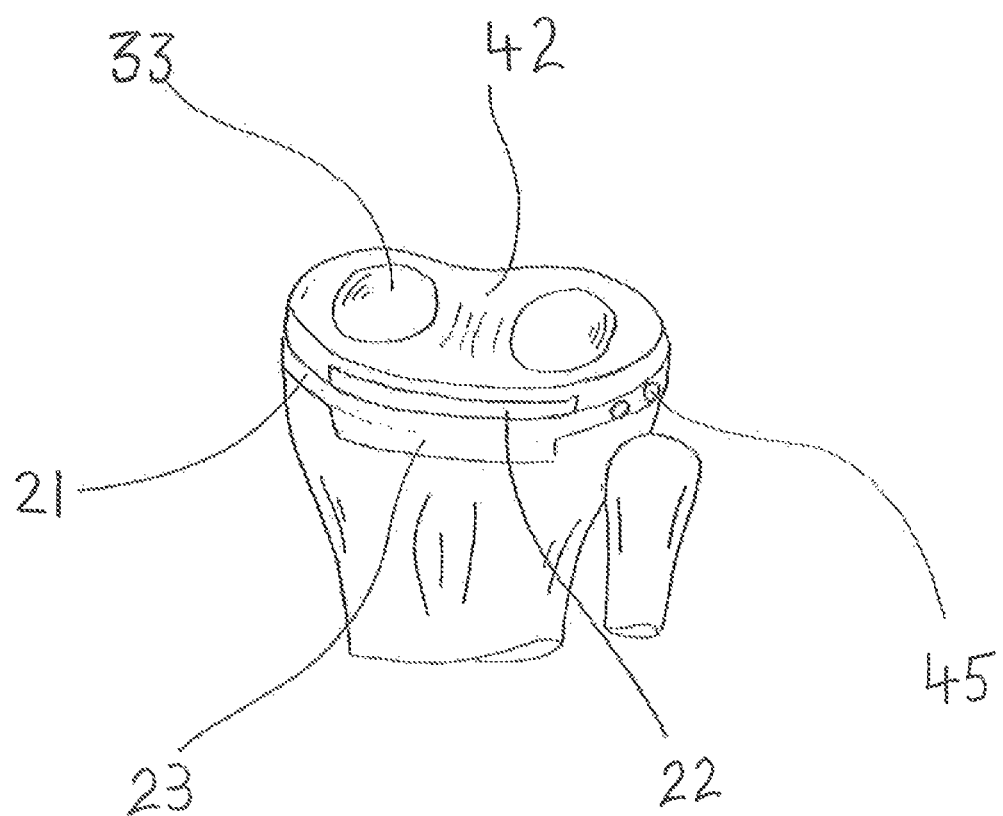
FIG. 10 is a perspective view of the polyethylene tray inserted in position onto the metallic tibial tray.
Figure 11:
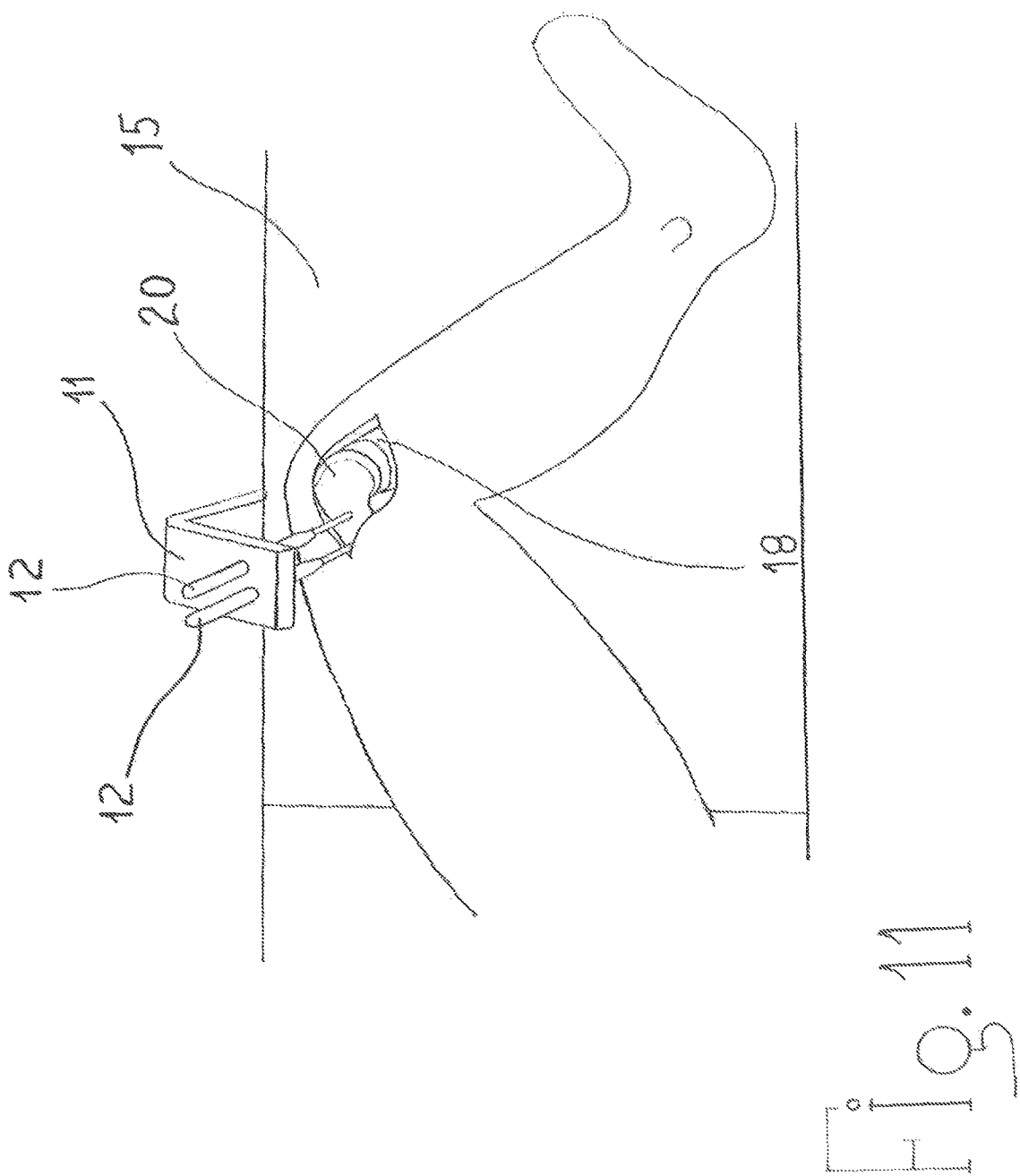
FIG. 11 is a perspective view of the operated femur secured to the operating table with two pins attached to the outrigger.

The tibial insert 42 is made of polyethylene and has the same shape and size of the tibial metallic tray as shown in FIG. 10. The top surface, which articulates with the femoral component, provides two cuples 33 or shallow condylar grooves that conformably match the condylar convex articular surfaces of the metallic femoral medial and lateral condyles.

The bottom of said polyethylene tibial insert has a groove configuration 41 that run transversely at the front of the polyethylene tibial insert and a similar transverse groove 41 runs at the back of the insert allowing said insert to slide conformably and easily between the two corresponding lips 22 and 43 of the metallic tibial tray 21 as shown in FIG. 7.

In addition, the polyethylene tibial tray 42 is locked in place using a small locking tab extending from the inferior surface of the polyethylene insert into a recess 44 situated at the lateral edge of the metallic tibial tray 21. Said tab when locked in place after lateral insertion will prevent it from moving out as shown in FIG. 9.

The metallic tibial tray 21 further provides two holes 45 at the side of said metallic tibial tray 21 which are used for insertion of a guiding tool and an impactor for seating said tibial tray in the proper position over the bony tibial plateau.

In a different embodiment of the present invention seen in FIG. 2, the retaining claws 2, 3, 4 and 5 (of FIG. 1) are replaced with central short mini posts 9 and 10 having a length between five and ten millimeters. Said mini posts 9, 10 being very short will not interfere with the insertion of the implant directly through the direct lateral approach but permit the operating surgeon to use conventional methylmetacrylate bone cement and insert and seat the bicondylar prosthesis anteriorly. The miniposts will prevent side migration of the implant. Furthermore, this method eliminates the need for displacement of the patella sideways and does not damage any adjacent soft tissue including the quadriceps tendon. In a different embodiment, the miniposts have a sharp pointed tip 57 to facilitate penetration into bone.

Figure 4:
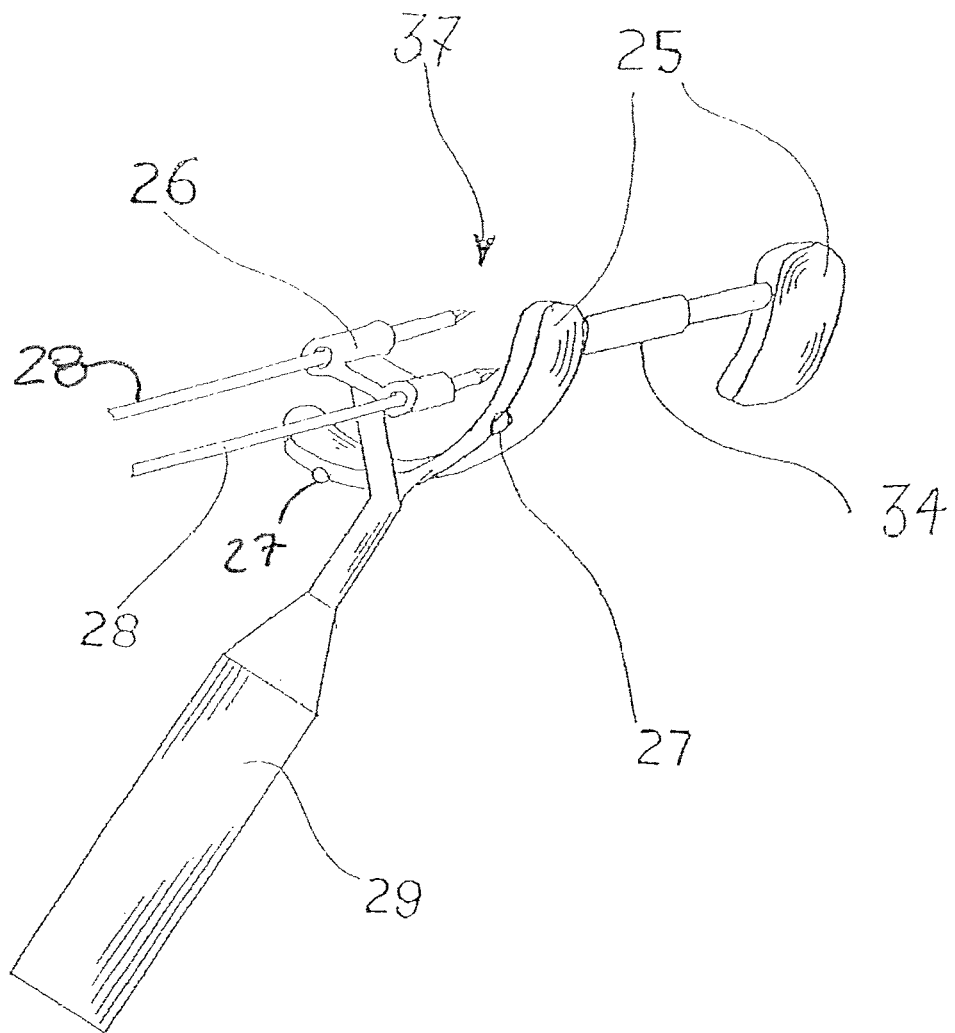
FIG. 4 is a perspective view of the hand held femoral template.
Figure 5:
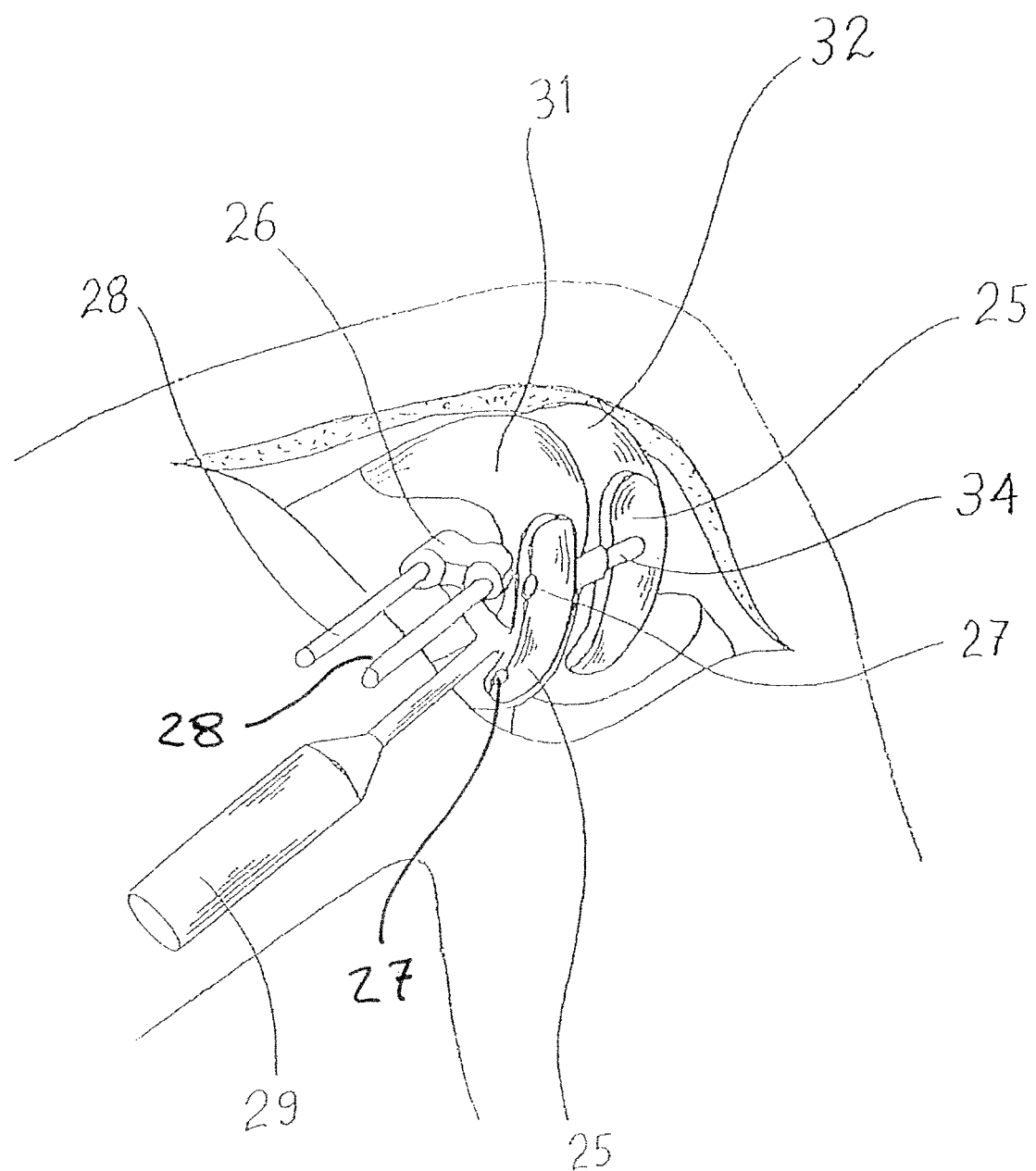
FIG. 5 is a perspective view of the hand held femoral template secured over the lateral condyle with two fixation pins.

In order to perform the bone resection, the operating surgeon must delineate the three resection planes, which will remove the weight bearing articular surface of the medial 32 and lateral 31 femoral condyles. A hand held femoral template 37 (FIG. 4) is used, which will allow the operating surgeon to precisely insert two template pins 28 over the lateral aspect of the distal femur at the proximal end of the incision, without the need to do a new skin incision. The hand held femoral template comprises two articular arcuate pads 25, connected together by adjustable connecting rod 34. Said pads are placed over the corresponding articular surfaces and manually held in place by handle 29 then firmly secured in place with two small pins introduced through holes 27.

Figure 6:
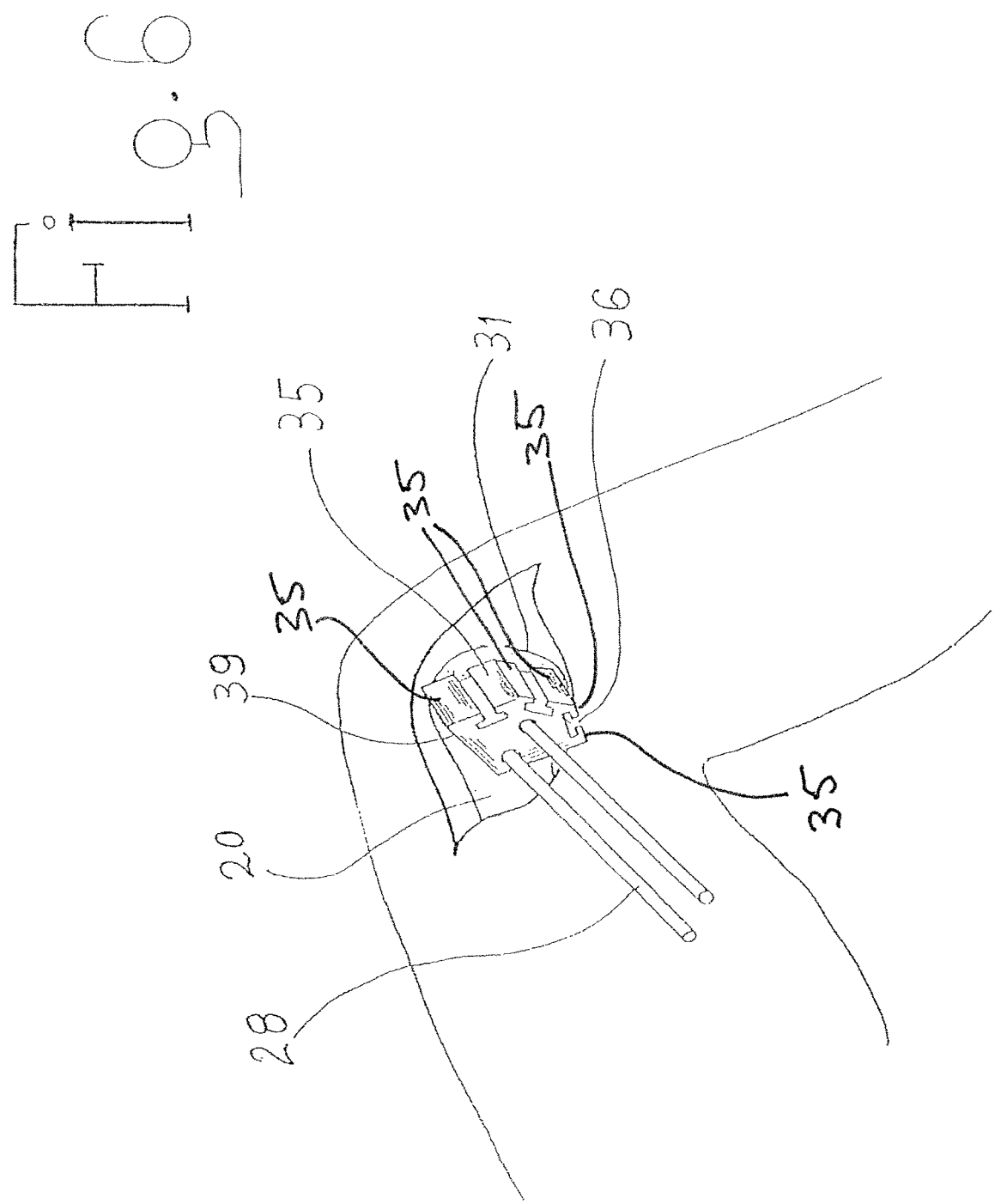
FIG. 6 is a perspective view of the polygonal cutting blocks secured over the lateral condyle with two fixation pins.

Subsequent to the precise placement of the hand held femoral template 37 and insertion of the two fixation pins 28, through bracket 26, the operating surgeon will withdraw the hand held femoral template 37 and then position the T slotted polygonal cutting blocks 39 over the two fixation pins and against the lateral surface of the distal femur (FIG. 6). Said T slotted cutting block 39 comprises flat surfaces 35 that correspond to the three flat surfaces of the concave non-articular surfaces 6 of the metallic femoral component.

As mentioned above, the resection of the femoral bone is advantageously performed by using the electromagnetic bone cutter unit 47, (FIG. 13) which is fully described in U.S. Pat. No. 8,167,883, of Zafer Termanini. Said electromagnetic driver 55 comprises an oscillating circular cutter 50 and has an inverted T shaped railing 48 at the bottom of the device in a form of an inverted T to guide its movement when said railing 48 slides into a T groove 36 located on the femoral and tibial cutting templates 39.

The accidental sliding of the oscillating circular cutter 50 beyond its intended bony target may cause soft tissue damage and disrupt major anatomical structures. In order to prevent such undesirable event, a conventional caliper or depth gage is used to measure the travel distance, which is equal to the width of the medial and lateral condyles Subsequently, a mechanical stop 46 in the form of a slidably movable bolt is applied on the rail 48 in order to restrict its travel beyond the desired resection point.

In a different embodiment of the present invention, the resection of the articular surfaces from the distal femur and the proximal tibia is performed using a robotic actuator 56 having at least four axis of freedom.

Said robotic actuator is situated on top of a rotating circular platform 54 situated on top of the outrigger 11 (FIG. 14). It is to be noted that the outrigger 11 is constructed of metal or durable plastic material, which withstands autoclave sterilization. Said outrigger is attached, over the drapes, to the side rails of the operating table after the appropriate sterile draping of the patient. Sterile clear plastic will cover the entire robotic actuator unit to preserve the surgical field sterility. The connection to a control module can be established with sterilizable cable connection or remotely without a cable connection using Wi-Fi or other wireless transmission well known in the art. A Power supply will then be provided using rechargeable battery pack unit 53 contained in the robotic actuator itself.

The robotic actuator is connected to a computer and monitor where DICOM from the pre-operative CT scan of the patient is retrieved allowing the registration of the registration of the actuator.

As in CNC machining, where the work piece is solidly fixed with a vise prior to milling, the distal femur is solidly fixed to the operating platform—using outrigger 11, attached via bracket to the side rails 14 of platform 15. After the resection of the articular surface of the distal femur is done, and the three flat surfaces are prepared 51 (FIG. 14), attention is then turned to preparation of the proximal tibia, which is then secured in similar fashion to the outrigger with two large fixation pins 12 as was for the femoral side. Subsequently, the proximal tibial surface is prepared by resecting the articular surface of the proximal tibia 18 using the electromagnetic bone cutter 50.

As opposed to prior art methods, using such as haptic technology or navigation, where the target objects such as bone is movable, in the present invention, the bone is firmly fixed and does not move. Furthermore, prior art navigation is basically used to align cutting guides. In the present invention, the actuator 56 will guide the electromagnetic bone cutter 50 to perform the bone cutting directly without the use of templates or cutting slotted guides (such as in FIG. 6).

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the forgoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed:

1. A method of forming a joint between a patient's femur and tibia, comprising the steps of:
    placing a patient on their side on an operating table and placing an operated leg on a platform generally horizontally placed between the patient's legs and firmly attached to side rails of the operating table;
    establishing an approach to a retropatellar region of the patient's knee joint;
    establishing locations of surfaces to be resected on the femur utilizing a hand held femoral template guide and a femoral cutting block;
    resecting a surface of the femur;
    resecting a surface of the tibia;
    inserting an implantable bicondylar femoral prosthesis having a curved articular portion that includes a medial condyle, a lateral condyle, and intercondylar anterior connection, the femoral prosthesis having inner retaining claws, such that when the femoral prosthesis is implanted on the femur, no portion of an outer surface of the femoral prosthesis resurfaces any area of the patello-femoral joint;
    inserting an implantable tibial prosthesis including a tibial platform having a bottom surface, which includes retaining ridges placed anteriorly and posteriorly onto said tibial platform, and a top surface, which includes anterior and posterior retaining ridges for retaining a polyethylene insert; and
    inserting the polyethylene insert having a bottom surface, which includes anterior and posterior grooves, by sliding said polyethylene insert into the retaining ridges of the top surface of the tibial platform.

2. The method of claim 1, wherein the operated leg is wrapped with surgical stockinet and firmly secured to an upper surface of the platform by heavy hook and loop fastener or a vacuum bean bag or a vise.

3. The method of claim 1, wherein the resection of the femur and the tibia is performed using an electromagnetic bone cutter.

4. The method of claim 3, wherein the electromagnetic bone cutter comprises an inverted T shaped rail running longitudinally along a bottom of said electromagnetic bone cutter, whereby movement of said electromagnetic bone cutter is thereby guided.

5. The method of claim 3, wherein the electromagnetic bone cutter is guided by the femoral cutting block having two or more T grooves adapted to slidably accept the inverted T shaped rail running longitudinally along the bottom of said electromagnetic bone cutter, whereby movement of said electromagnetic bone cutter is thereby guided during the resection, the femoral cutting block being removably affixed to a lateral surface of the femur and secured in position using at least two fixation pins, wherein the fixation pins pass through the femoral cutting block and into said femur, positions of the fixation pins relative to the femur being established by the hand held femoral template guide.

6. The method in claim 5, wherein the femoral cutting block is a template for the electromagnetic bone cutter, and establishes resection planes for removal of weight bearing articular surfaces of medial and lateral condyles of the femur, the femoral cutting block comprising three flat surfaces which correspond to three flat surfaces of non-articular surfaces of the femoral prosthesis.

7. The method of claim 5, wherein the hand held femoral template guide; comprises a handle, two arcuate and curved medial and lateral condylar templates connected by a sliding connecting rod, and a bracket having apertures for receiving the fixation pins, wherein, in use, the arcuate and curved medial and lateral condylar templates are positioned against medial and lateral condyles of the femur, fixation pins are inserted through the apertures, ends of the fixation pins are removably affixed to the femur, subsequently the hand held femoral template guide is disengaged from the fixation pins, and thereafter the femoral cutting block is engaged upon the fixation pins.

* * * * *